United States Patent
Keller

(10) Patent No.: US 7,927,337 B2
(45) Date of Patent: Apr. 19, 2011

(54) BONE SEPARATOR

(75) Inventor: Arnold Keller, Kayhude (DE)

(73) Assignee: NuVasive, Inc., San Diego, CA (US)

( * ) Notice: Subject to any disclaimer, the term of this patent is extended or adjusted under 35 U.S.C. 154(b) by 9 days.

(21) Appl. No.: 10/567,966

(22) PCT Filed: Apr. 5, 2005

(86) PCT No.: PCT/EP2005/003576
§ 371 (c)(1),
(2), (4) Date: Feb. 10, 2006

(87) PCT Pub. No.: WO2005/099589
PCT Pub. Date: Oct. 27, 2005

(65) Prior Publication Data
US 2006/0235422 A1     Oct. 19, 2006

(30) Foreign Application Priority Data

Apr. 19, 2004   (DE) .......................... 10 2004 018 872

(51) Int. Cl.
*A61B 17/70* (2006.01)
(52) U.S. Cl. .......................................... 606/90
(58) Field of Classification Search .................. 606/90, 606/86, 53, 105, 246, 251, 252, 257, 258; 403/154, 330; 600/201; 70/2, 18
See application file for complete search history.

(56) References Cited

U.S. PATENT DOCUMENTS

| | | | |
|---|---|---|---|
| 4,475,546 A * | 10/1984 | Patton | 606/57 |
| 4,827,918 A * | 5/1989 | Olerud | 606/258 |
| 4,957,495 A | 9/1990 | Kluger | |
| 6,036,691 A * | 3/2000 | Richardson | 606/57 |
| 6,340,363 B1 | 1/2002 | Bolger et al. | |
| 6,729,515 B2 * | 5/2004 | Nicosia et al. | 224/413 |
| 7,011,658 B2 * | 3/2006 | Young | 606/61 |
| 2003/0187436 A1 | 10/2003 | Bolger et al. | |

FOREIGN PATENT DOCUMENTS

| | | |
|---|---|---|
| DE | 4201043 | 7/1993 |
| JP | 2001-1129108 | 5/2001 |
| SU | 1463250 | 3/1989 |
| SU | 1630797 A1 | 2/1991 |
| WO | WO-03/024344 | 3/2003 |

OTHER PUBLICATIONS

English translation of IPRP directed to counterpart application No. PCT/EP2005/003576.
Notification of Reasons for Refusal in the counterpart Japanese Patent Application No. 2007/507698 dated Sep. 14, 2010. EN translation is attached.

* cited by examiner

*Primary Examiner* — Eduardo C Robert
*Assistant Examiner* — David Comstock
(74) *Attorney, Agent, or Firm* — Jonathan Spangler; Marjorie Jarris

(57) ABSTRACT

A bone spreader includes two tubular pin holders which are connected to one another by a parallel guide system, and two pins that are configured to be connected to the bone parts that are to be spread apart. In order to give the bone parts that are to be spread apart a more secure position in relation to one another, at least one of the pin holders is provided with a locking device for a pin located in the pin holder. This locking device includes a locking finger which is movable tangentially with respect to the pin holder and which, in the locking position, engages in a transverse groove of the associated pin and can be formed by a pivotably mounted hook.

6 Claims, 1 Drawing Sheet

BONE SEPARATOR

FIELD AND BACKGROUND OF THE INVENTION

The invention relates to a bone spreader for spreading bone parts apart including two parallel tubular pin holders, which are connected to one another by a parallel guide system, and two pins to be connected to the bone parts that are to be spread apart. In connection with the invention, this term also includes screws. The pins are introduced parallel to one another into the bone parts that are to be spread apart. Their free sections are introduced into the pin holders. When these are now moved away from one another or moved closer to one another by means of the parallel guide system, this movement is transmitted to the bone parts. This type of spreader is especially suitable for distraction of two cervical vertebral bodies for the purpose of implantation of a cervical intervertebral prosthesis, as the vertebral bodies are guided parallel to one another during the distraction. However, this parallel attribute applies only with respect to the direction of the pin holders. Two degrees of freedom remain. These are, on the one hand, a rotation of the bone parts about the pin axis, which for various reasons is of no consequence in normal circumstances, and, on the other hand, a displacement in the direction of the pin holders, which displacement can be prevented by a locking device. For this purpose, a first known design of this locking device, disclosed in WO03/024344, uses a friction clamp, which in many cases is not secure enough. A second known design, disclosed in U.S. Pat. No. 6,340,363, uses a clamping screw or some kind of clamp. A clamping screw, however, cannot be maneuvered, or may be maneuvered only with difficulty, deep within the operating site. The issue remains, furthermore, of how a clamp can be designed so that it is both secure and easy to operate.

SUMMARY OF THE INVENTION

According to the invention, this disadvantage is remedied by the fact that the locking device is designed in the form of a locking finger which is guided between a locking position and a release position in a transverse movement tangentially with respect to the pin holder and at least one transverse groove in the pin, into which groove the locking finger engages in the locking position. Several transverse grooves may also be provided, one of which is chosen for the engagement of the locking finger. To ensure that the locking finger cannot be lost as a separate part, according to a further feature of the invention, it is designed as a hook which is mounted so as to be pivotable about an axis extending approximately parallel to the pin holder. The arrangement is especially simple and clear if the hook is arranged at the open end of the pin holder closer to the parallel guide system.

BRIEF DESCRIPTION OF THE DRAWINGS

The invention is explained in more detail below with reference to the drawing which depicts an advantageous illustrative embodiment and in which.

DETAILED DESCRIPTION OF THE INVENTION

Figure 1:
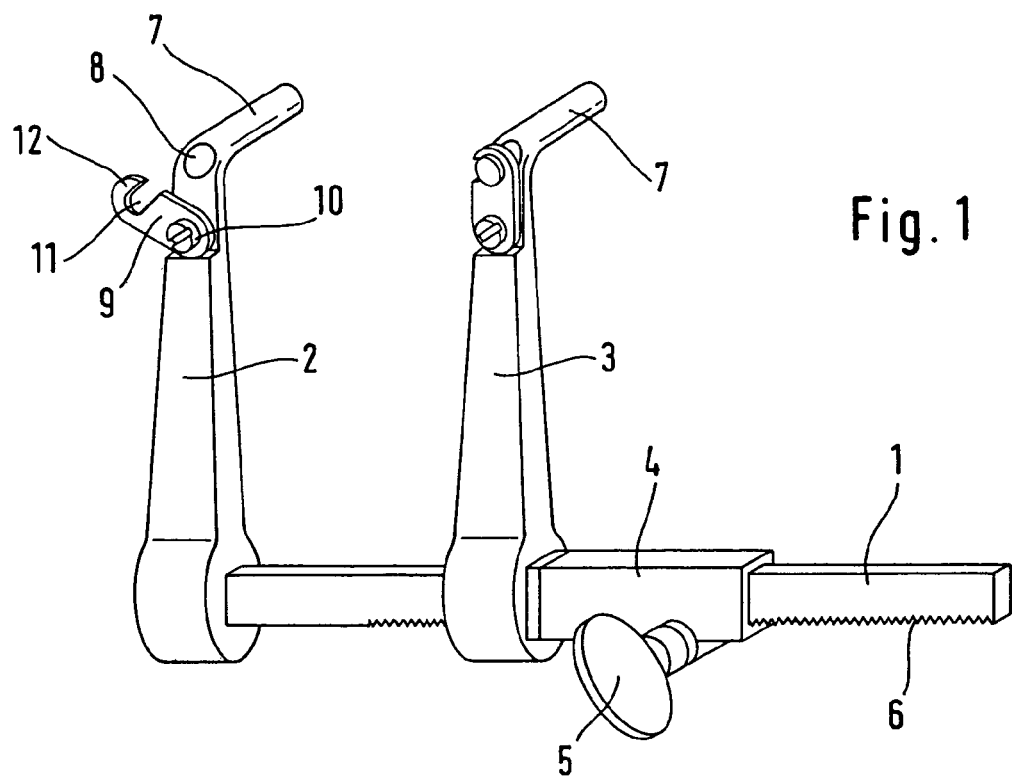
FIG. 1 shows an overall view of the spreader.

A first spreader body 2 is arranged rigidly at the end of a guide bar 1 of noncircular cross section. A second spreader body 3 with a guide tube 4 is arranged parallel to the spreader body 2 on the guide bar 1 and is displaceable in the longitudinal direction of said guide bar 1, but not rotatable. The displacement is effected using a toggle 5 which is connected to a pinion (not shown) engaging in a toothing 6 of the guide bar 1. In addition, any kind of locking means can be connected to the spreader body 3 or to the guide tube 4 so as to secure the distance between the spreader bodies 2 and 3.

Arranged at the free ends of the spreader bodies 2 and 3 there are tubular pin holders 7 which are set at an angle in relation to the spreader bodies 2, 3. They extend parallel to one another in planes which are perpendicular to the guide bar. They are used for receiving two pins, each one of which is connected respectively to one of the two bones or fragments that are to be distracted. By operating the toggle 5, it is possible for these bone parts or fragments to be spread apart from one another or guided toward one another, in which process they are held parallel to one another in relation to the axes of the two pin holders 7. To this extent, the bone spreader can be regarded as being known.

Whereas in known bone spreaders of this kind the hole inside the pin holder is closed at the rear end connected to the associated spreader body 2, 3, according to the invention, it is continued right through at this location, such that it opens out at 8. Adjacent to the opening 8, a hook plate 9 is mounted pivotably by way of a screw 10. It lies in a plane extending substantially perpendicular to the axis of the pin holder. It contains a hook cutout 11 which is outwardly delimited by a hook finger 12 whose direction extends tangentially with respect to the axis of the pin holder.

Figures 2, 3:
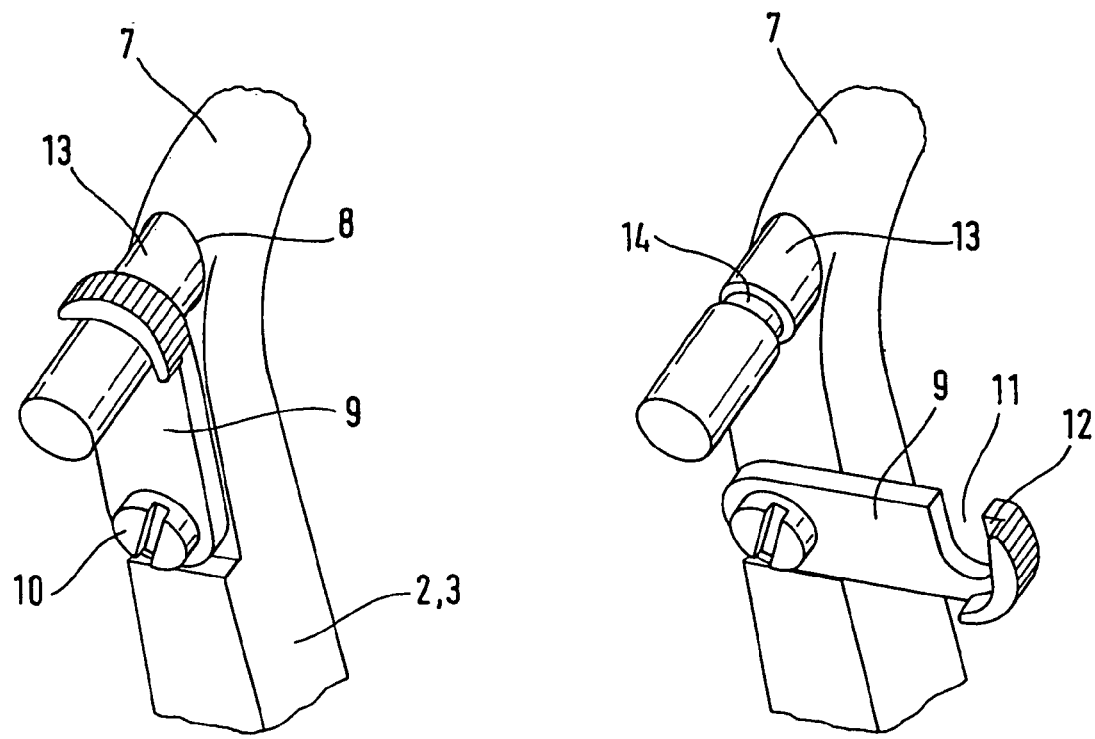
FIGS. 2 and 3 show partial views of the spreader in different stages of its operation.

The associated pins 13 have, at least at their rear end, one or more peripheral grooves 14 whose width (measured in the longitudinal direction of the pin) is slightly greater than the thickness of the plate 9 or hook finger 12. When a pin is located in the pin holder in such a way that its rear end protrudes outward at the rear, as is shown in FIG. 2, the plate 9 can be pivoted in such a way that the hook finger 12 engages in one of the grooves 14 and in this position, which is illustrated in FIG. 3, prevents the pin 13 from moving in its longitudinal direction.

The hook finger 12 can be designed such that it locks in the closed position (FIGS. 1 and 3) so as not to inadvertently come loose from here under the action of slight forces. Instead of this, or in addition, the pivot bearing of the plate 9 can be provided with a spring or catch mechanism which satisfies this purpose.

The invention has the effect that the pins received in the pin holders 7 can be secured in the pin holder by means of a rapid and simple movement by the operator. In this way, the secured bone parts are prevented from executing a relative movement in the direction of the pin holders.

The invention claimed is:

1. A bone spreader for spreading bones apart, comprising:
a parallel guide system with a guide bar having a noncircular cross section;
a first pin and a second pin;
a first tubular pin holder and a second tubular pin holder connected to one another by the parallel guide system, the first and second tubular pin holders configured to receive the first pin and second pin, respectively, couple adjacent to the bone parts that are to be spread apart to the parallel guide system, and at least one of the first and second tubular pin holders being arranged rigidly on the guide bar to guide parallel displacement of the bones, and having a locking device for a respective one of the first and second pins after being positioned therethrough; and wherein the first and second pins each have at least one transverse groove formed therein, the locking device includes a locking finger which is guided between a locking position and a release position in a transverse movement tangentially with respect to the tubular pin holder, the locking finger being configured to engage in the groove in the locking position, and the tubular pin holders are arranged in planes which are perpendicular to the guide bar.

2. The bone spreader as claimed in claim 1, wherein the locking finger is in the form of a hook which is mounted at an open end of the tubular pin holder closer to the parallel guide system and is pivotable about an axis extending approximately parallel to said tubular pin holder.

3. A method for spreading bone parts apart comprising:
introducing a first pin into a first bone part and a second pin into a second bone part;
introducing a free end of the first pin into a first tubular pin holder of a parallel guide system;
introducing a free end of the second pin into a second tubular pin holder of the parallel guide system;
securing the free end of the first pin to the first tubular pin holder with a first locking device;
moving the first and second pins relative to one another by operation of the parallel guide system to spread apart the first and second bone parts; and
implanting an intervertebral prosthesis between the first and second bone parts.

4. The method of claim 3, further comprising:
securing the free end of the of the second pin to the second tubular pin holder with a second locking device.

5. The method of claim 3, wherein the first pin includes at least one transverse groove.

6. The method of claim 3, wherein the first locking device is a locking finger.

* * * * *

UNITED STATES PATENT AND TRADEMARK OFFICE
CERTIFICATE OF CORRECTION

PATENT NO. : 7,927,337 B2
APPLICATION NO. : 10/567966
DATED : April 19, 2011
INVENTOR(S) : Arnold Keller It is certified that error appears in the above-identified patent and that said Letters Patent is hereby corrected as shown below:

On the cover page of the patent, item (73), Assignee name, please delete "NuVasive Inc." and replace with --Cervitech, Inc.--

In Claim 1, column 2, lines 60-61, please delete "couple adjacent to the bone parts" and replace with --to couple adjacent bone parts--.

Signed and Sealed this
Twentieth Day of September, 2011

David J. Kappos
*Director of the United States Patent and Trademark Office*